(12) United States Patent
Chen et al.

(10) Patent No.: US 6,861,573 B2
(45) Date of Patent: Mar. 1, 2005

(54) ISOLATED NUCLEIC ACID MOLECULE ENCODING A GLYCINE-RICH POLYPEPTIDE

(75) Inventors: Chao-Ying Chen, No. 1, Sec. 4, Roosevelt Rd., Taipei (TW); Yu-Yen Lu, Taipei (TW)

(73) Assignee: Chao-Ying Chen, Taipei (TW)

( * ) Notice: Subject to any disclaimer, the term of this patent is extended or adjusted under 35 U.S.C. 154(b) by 0 days.

(21) Appl. No.: 10/190,902

(22) Filed: Jul. 8, 2002

(65) Prior Publication Data

US 2004/0006786 A1 Jan. 8, 2004

(51) Int. Cl.[7] .................. C12N 15/09; C12N 15/29; C12N 15/82; A01H 5/00
(52) U.S. Cl. .................. 800/279; 800/298; 800/295; 435/320.1; 435/468; 536/23.6
(58) Field of Search .................. 800/278, 279, 800/298, 295; 536/23.6, 24.1

(56) References Cited

PUBLICATIONS

J.A. Ryals, et al. "Systemic Acquired Resistance" *The Plant Cell*, vol. 8, p. 1809–1819, (1996).
H. Kessmann, et al. "Induction of Systemic Acquired Disease Resistance in Plants by Chemicals" *Annu. Rev. Phytopathol.*, vol. 32, p. 439–459, (1994).
J–P Metraux, "Systemic acquired resistance and salicyclic acid: current state of knowledge" *European Journal of Plant Pathology*, vol. 10, p. 13–18, (2001).
N. Midoh, et al. "Expression of Defense–related Genes by Probenazole or 1, 2–Benzisothiazole–3(2H)–one 1, 1–dioxide" *J. Pesticide Sci.*, vol. 22, p. 45–47, (1997).
K. Yoshioka, et al. "Probenazole induces systemic acquired resistance in *Arabidopsis* with a novel type of action" *The Plant Journal*, vol. 25, No. 2, p. 149–157, (2001).
G.N. Agrios, "How Pathogens Attack Plants" Plant Pathology, Chapter Three, p. 63–65, 72, 97–98, 103–104, (1997), Academic Press.
A.M. Showalter, "Structure and Function of Plant Cell Wall Proteins" *The Plant Cell*, vol. 5, p. 9–23, (1993).
A. Molina, et al. "Differential expression of pathogen–responsive genes encoding two types of glycine–rich proteins in barley" *Plant Molecular Biology*, vol. 33, p. 803–810, (1997).
H. Harrak, et al., "A Proline–, Threonine–, and Glycine–Rich Protein Down–regulated by Drought Is Localized . . . Elements" *Plant Physiology*, vol. 121, p. 557–564, (1999).
10th Int'l Congress on Molecular Plant–Microbe Interactions: Abstracts # 313, 314, 315, (2001).

*Primary Examiner*—Medina A. Ibrahim
(74) *Attorney, Agent, or Firm*—Ladas & Parry LLP (57) ABSTRACT

The present invention relates to a new gene encoding a glycine-rich polypeptide, and an expression vector, host cell and transgenic plant comprising the gene. The expression of the gene of the invention in the plant will enhance resistance against a wide variety of pathogens, in particular fungi.

11 Claims, 7 Drawing Sheets

A  B

Control lily cDNA probe      SA-treated lily cDNA probe

```
  1   ATGGCTTCTAAGGCTCTTCTCATGTTGGGTGTTCTCATTGTGGCT
       M  A  S  K  A  L  L  M  L  G  V  L  I  V  A
 46   GCACTATTTGTCACCTCCGACGCTGGTCGGGAGCTGGCTGAGGAA
       A  L  F  V  T  S  D  A↓ G  R  E  L  A  E  E
 91   ACAAAGGAAAACACTGAAAGAGGGCAACCGAGGCAGGAGTTGCC
       T  K  E  N  T  E  K  R  A  T  E  A  G  V  A
136   GACCAGAAGTACGGTGGCGGCTACAACAACGGTGGTGGTTACCCA
       D  Q  K  Y  G  G  G  Y  N  N  G  G  Y  P
181   GGAGGCGGCGGTGGATACCACAATGGTGGTGGTTATCCAGGAGGA
       G  G  G  G  Y  H  N  G  G  G  Y  P  G  G
226   GGTGGTGGATATCCAGGAGGAGGCGGTGGTTACCCTGGGGGAGGA
       G  G  G  Y  P  G  G  G  G  Y  P  G  G  G
271   GGAGGGTACCACAATGGTGGTGGCGGCGGACGCTGCTACAACGGT
                                              ←
       G  G  Y  H  N  G  G  G  G  R  C  Y  N  G
316   TGCTGCCGTCGCGGATACTATGGTGGCTGCCGGTGCTGCGCCCAC
       C  C  R  R  G  Y  Y  G  G  C  R  C  C  A  H
361   CCCGATGAGATCCCGGACCCTGAATACCGCGCTGAGCCTGCTTAT
       P  D  E  I  P  D  P  E  Y  R  A  E  P  A  Y
```

Fig. 3A

```
TGACACCCATAGGGGTTTAATTAGATTTGGCTTCCCATGGTTGCC
  G   H   P   *
```

451
```
TGGTCTGATGTATAAGGAGTGATTGAGGGAACTTATGTGTGGAAA
```

496
```
AGATGCGTGGTTTGATGCAGAAGAGTGATCGAAGGAACTTATGT
```

541
```
AAAAATAAAAGGAAATAATGTTTCTGCTTAAGTTGTATTATTC
```

506
```
AGTGTTTATATATACAAGTATGACCCTGCACATGATGTGCGGTGG
```

631    ATAAATTAT

SEQUENCE LISTING

<160> NUMBER OF SEQ ID NOS: 13

<210> SEQ ID NO 1
<211> LENGTH: 639
<212> TYPE: DNA
<213> ORGANISM: Lilium
<220> FEATURE:
<221> NAME/KEY: CDS
<222> LOCATION: (1)..(417)
<223> OTHER INFORMATION:

<400> SEQUENCE: 1

```
atg gct tct aag gct ctt ctc atg ttg ggt gtt ctc att gtg gct gca      48
Met Ala Ser Lys Ala Leu Leu Met Leu Gly Val Leu Ile Val Ala Ala
1               5                   10                  15 cta ttt gtc acc tcc gac gct ggt cgg gag ctg gct gag gaa aca aag      96
Leu Phe Val Thr Ser Asp Ala Gly Arg Glu Leu Ala Glu Glu Thr Lys
                20                  25                  30 gaa aac act gaa aag agg gca acc gag gca gga gtt gcc gac cag aag     144
Glu Asn Thr Glu Lys Arg Ala Thr Glu Ala Gly Val Ala Asp Gln Lys
            35                  40                  45 tac ggt ggc ggc tac aac aac ggt ggt ggt tac cca gga ggc ggc ggt     192
Tyr Gly Gly Gly Tyr Asn Asn Gly Gly Gly Tyr Pro Gly Gly Gly Gly
        50                  55                  60 gga tac cac aat ggt ggt ggt tat cca gga gga ggt ggt gga tat cca     240
Gly Tyr His Asn Gly Gly Gly Tyr Pro Gly Gly Gly Gly Gly Tyr Pro
65                  70                  75                  80 gga gga ggc ggt ggt tac cct ggg gga gga gga ggg tac cac aat ggt     288
Gly Gly Gly Gly Gly Tyr Pro Gly Gly Gly Gly Tyr His Asn Gly
                85                  90                  95 ggt ggc ggc gga cgc tgc tac aac ggt tgc tgc cgt cgc gga tac tat     336
Gly Gly Gly Gly Arg Cys Tyr Asn Gly Cys Cys Arg Arg Gly Tyr Tyr
            100                 105                 110 ggt ggc tgc cgg tgc tgc gcc cac ccc gat gag atc ccg gac cct gaa     384
Gly Gly Cys Arg Cys Cys Ala His Pro Asp Glu Ile Pro Asp Pro Glu
        115                 120                 125 tac cgc gct gag cct gct tat gga cac cca tag ggtttaatt agatttggct   437
Tyr Arg Ala Glu Pro Ala Tyr Gly His Pro
    130                 135 tcccatggtt gcctggtctg atgtataagg agtgattgag ggaacttatg tgtggaaaag   497
atgcgtggtt tgatgcagaa agagtgatcg aaggaactta tgtaaaaata aaaggaaat    557 aatgtttcct gcttaagttg tattattcag tgtttatata tacaagtatg accctgcaca   617
tgatgtgcgg tggataaatt at                                            639
```

<210> SEQ ID NO 2
<211> LENGTH: 138
<212> TYPE: PRT
<213> ORGANISM: Lilium

<400> SEQUENCE: 2

```
Met Ala Ser Lys Ala Leu Leu Met Leu Gly Val Leu Ile Val Ala Ala
1               5                   10                  15

Leu Phe Val Thr Ser Asp Ala Gly Arg Glu Leu Ala Glu Glu Thr Lys
                20                  25                  30

Glu Asn Thr Glu Lys Arg Ala Thr Glu Ala Gly Val Ala Asp Gln Lys
            35                  40                  45

Tyr Gly Gly Gly Tyr Asn Asn Gly Gly Gly Tyr Pro Gly Gly Gly Gly
        50                  55                  60
```

```
Gly Tyr His Asn Gly Gly Gly Tyr Pro Gly Gly Gly Gly Tyr Pro
 65                  70                  75                  80

Gly Gly Gly Gly Tyr Pro Gly Gly Gly Gly Tyr His Asn Gly
                 85                  90                  95

Gly Gly Gly Arg Cys Tyr Asn Gly Cys Cys Arg Gly Tyr Tyr
            100                 105                 110

Gly Gly Cys Arg Cys Ala His Pro Asp Glu Ile Pro Asp Pro Glu
            115                 120                 125

Tyr Arg Ala Glu Pro Ala Tyr Gly His Pro
    130                 135
```

<210> SEQ ID NO 3
<211> LENGTH: 64
<212> TYPE: PRT
<213> ORGANISM: Hordeum vulgare

<400> SEQUENCE: 3

```
Pro Gly His Gly Gly Lys Gly Gly Gly Tyr Pro Gly His Gly Gly
 1               5                  10                  15

Gly Gly Gly Gly Tyr Pro Gly His Gly Gly Ser Ser Gly Cys
                20                  25                  30

His Trp Gly Cys Cys Gly His Gly Tyr Asn Gly Cys Arg Cys Ala
            35                  40                  45

Arg Ala Asp Glu Val Pro Glu Pro Met Tyr Arg Ala Glu Val Arg Asn
    50                  55                  60
```

<210> SEQ ID NO 4
<211> LENGTH: 145
<212> TYPE: PRT
<213> ORGANISM: Arabidopsis thaliana

<400> SEQUENCE: 4

```
Met Ala Ser Lys Ala Leu Val Leu Leu Gly Leu Glu Ala Val Leu Leu
 1               5                  10                  15

Val Val Ser Glu Val Ala Ala Ala Ser Ser Ala Thr Val Asn Ser Glu
                20                  25                  30

Ser Lys Glu Thr Val Lys Pro Asp Gln Arg Gly Tyr Gly Asp Asn Gly
                35                  40                  45

Gly Asn Tyr Asn Asn Gly Gly Tyr Gln Gly Gly Gly Asn Tyr
    50                  55                  60

Gln Gly Gly Gly Gly Asn Tyr Gln Gly Gly Gly Asn Tyr Gln Gly
 65                  70                  75                  80

Gly Gly Gly Arg Tyr Gln Gly Gly Gly Arg Tyr Gln Gly Gly
                85                  90                  95

Gly Arg Tyr Gln Gly Gly Gly Gly Arg Gln Gly Gly Gly Ser Arg
            100                 105                 110

Gly Ser Tyr Cys Arg His Gly Cys Cys Tyr Arg Gly Tyr Asn Gly Cys
            115                 120                 125

Ser Arg Cys Cys Ser Tyr Ala Gly Glu Ala Val Gln Thr Gln Pro Gly
            130                 135                 140

His
145
```

<210> SEQ ID NO 5
<211> LENGTH: 135
<212> TYPE: PRT

<213> ORGANISM: Arabidopsis thaliana

<400> SEQUENCE: 5

Met Ala Ser Lys Ala Leu Leu Phe Leu Ser Leu Ile Val Val Leu Leu
1               5                   10                  15

Ile Ala Ser Glu Val Val Ala Arg Asp Leu Ala Glu Lys Ser Ala Glu
            20                  25                  30

Gln Lys Asn Asn Glu Arg Asp Glu Val Lys Gln Thr Glu Gln Phe Gly
        35                  40                  45

Gly Phe Pro Gly Gly Gly Tyr Gly Gly Phe Pro Gly Gly Gly Tyr Gly
    50                  55                  60

Gly Asn Pro Gly Gly Gly Tyr Gly Asn Arg Gly Gly Gly Tyr Arg Asn
65                  70                  75                  80

Arg Asp Gly Gly Tyr Gly Asn Arg Gly Gly Tyr Gly Asn Arg Gly
                85                  90                  95

Gly Gly Tyr Cys Arg Tyr Gly Cys Cys Tyr Arg Gly Tyr Tyr Gly Gly
            100                 105                 110

Cys Phe Arg Cys Cys Ala Tyr Ala Gly Gln Ala Val Gln Thr Gln Pro
        115                 120                 125

Gln Ser Thr Glu Pro Gly His
    130                 135

210> SEQ ID NO 6
211> LENGTH: 109
<212> TYPE: PRT
<213> ORGANISM: Nicotiana tabacum

<400> SEQUENCE: 6

Met Gly Ser Lys Ala Phe Leu Phe Leu Gly Leu Cys Leu Ala Phe Phe
1               5                   10                  15

Phe Leu Ile Ser Ser Glu Val Val Ala Gly Glu Leu Ala Glu Thr Ser
            20                  25                  30

Asn Pro Met Lys Leu Asp Gly Glu Asn Gly Val Asp Val Asp Gly Arg
        35                  40                  45

Gly Gly Tyr Asn Asp Val Gly Gly Asp Gly Tyr Tyr Gly Gly Gly Arg
    50                  55                  60

Gly Arg Gly Gly Gly Tyr Lys Arg Arg Gly Cys Arg Tyr Gly Cys
65                  70                  75                  80

Cys Arg Lys Gly Tyr Asn Gly Cys Lys Arg Cys Cys Ser Tyr Ala Gly
            85                  90                  95

Glu Ala Met Asp Lys Val Thr Glu Ala Gln Pro His Asn
            100                 105

<210> SEQ ID NO 7
<211> LENGTH: 144
<212> TYPE: PRT
<213> ORGANISM: Chenopodium rubrum

<400> SEQUENCE: 7

Met Gly Ser Lys Ile Phe Leu Leu Gly Leu Ser Ile Ala Phe Ala
1               5                   10                  15

Ile Leu Ile Ser Ser Glu Val Ala Ala Arg Glu Leu Ala Glu Thr Ala
            20                  25                  30

Ala Lys Thr Glu Gly Tyr Asn Asn Gly Gly Tyr His Asn Gly Gly
        35                  40                  45

Gly Gly Tyr Asn Asn Gly Gly Gly Tyr His Asn Gly Gly Gly Gly Tyr

```
                    50                  55                  60
Asn Asn Gly Gly Gly Tyr His Asn Gly Gly Gly Tyr Asn Asn Gly
 65                  70                  75                  80

Gly Gly Tyr Asn His Gly Gly Gly Tyr Asn Asn Gly Gly Gly His
                    85                  90                  95

His Asn Gly Gly Gly Gly Tyr Asn Asn Gly Gly Tyr His Gly Gly
                100                 105                 110

Gly Gly Ser Cys Tyr His Tyr Cys His Gly Arg Cys Cys Ser Ala Ala
            115                 120                 125

Glu Ala Lys Ala Leu Glu Ala Thr Thr Ala Gln Val Lys Pro Gln Asn
        130                 135                 140

<210> SEQ ID NO 8
<211> LENGTH: 144
<212> TYPE: PRT
<213> ORGANISM: Daucus carota

<400> SEQUENCE: 8

Met Gly Ser Lys Ile Phe Leu Leu Gly Leu Ser Ile Ala Phe Ala
 1               5                  10                  15

Ile Leu Ile Ser Ser Glu Val Ala Ala Arg Glu Leu Ala Glu Thr Ala
                20                  25                  30

Ala Lys Thr Glu Gly Tyr Asn Asn Gly Gly Tyr His Asn Gly Gly
            35                  40                  45

Gly Gly Tyr Asn Asn Gly Gly Tyr His Asn Gly Gly Gly Gly Tyr
        50                  55                  60

Asn Asn Gly Gly Gly Tyr His Asn Gly Gly Gly Tyr Asn Asn Gly
 65                  70                  75                  80

Gly Gly Tyr His Asn Gly Gly Gly Tyr Asn Asn Gly Gly Gly His
                85                  90                  95

His Asn Gly Gly Gly Gly Tyr Asn Asn Gly Gly His His Gly Gly
                100                 105                 110

Gly Gly Ser Cys Tyr His Tyr Cys His Gly Arg Cys Cys Ser Ala Ala
            115                 120                 125

Glu Ala Lys Ala Leu Glu Ala Thr Thr Ala Gln Val Lys Pro Gln Asn
        130                 135                 140

<210> SEQ ID NO 9
<211> LENGTH: 129
<212> TYPE: PRT
<213> ORGANISM: Pisum sativum

<400> SEQUENCE: 9

Met Asp Ser Arg Lys Ala Met Leu Ile Leu Gly Leu Leu Ala Met Val
 1               5                  10                  15

Leu Leu Ile Ser Ser Glu Val Ser Ala Arg Glu Leu Thr Glu Glu Val
                20                  25                  30

Val Glu Lys Ser Asp Glu Val Asn Asp Ala Lys Tyr Gly Gly Tyr Gly
            35                  40                  45

Arg Gly Gly Gly Tyr His Gly Gly Gly Tyr His Asn Gly Gly Gly
        50                  55                  60

Gly Tyr Asn Gly Gly Gly Gly Tyr His Asn Gly Gly Gly Tyr Asn
 65                  70                  75                  80

Gly Gly Gly Gly Tyr His Asn Gly Gly Gly Tyr His Asn Gly Gly
                85                  90                  95

Gly Gly Tyr Asn Gly Gly Gly Gly Tyr His Asn Gly Gly Gly Tyr
```

```
                    100                 105                 110
His Gly Gly Gly His Gly Gly His Gly Gly Ala Ser Asn Asn Gly
            115                 120                 125

Asn

<210> SEQ ID NO 10
<211> LENGTH: 159
<212> TYPE: PRT
<213> ORGANISM: Medicago sativa

<400> SEQUENCE: 10

Met Val Leu Leu Ile Ser Ser Glu Val Ser Ala Arg Asp Leu Thr Glu
1               5                   10                  15

Thr Thr Ser Asp Ala Lys Lys Glu Val Glu Lys Thr Asn Glu Val
            20                  25                  30

Asn Asp Ala Lys Tyr Gly Gly Gly Tyr Asn His Gly Gly Gly Tyr
            35                  40                  45

Asn Gly Gly Gly Tyr Asn His Gly Gly Gly Tyr Asn Asn Gly Gly
        50                  55                  60

Gly Tyr Asn His Gly Gly Gly Tyr Asn Asn Gly Gly Gly Tyr
65                  70                  75                  80

Asn His Gly Gly Gly Tyr Asn Asn Gly Gly Gly Tyr Asn His
                85                  90                  95

Gly Gly Gly Gly Tyr Asn Asn Gly Gly Gly Tyr Asn His Gly Gly
            100                 105                 110

Gly Gly Tyr Asn Gly Gly Tyr Asn His Gly Gly Gly Tyr Asn
        115                 120                 125

His Gly Gly Gly Cys Gln Tyr His Cys His Gly Arg Cys Cys Ser
        130                 135                 140

His Ala Glu Phe Val Ala Met Gln Ala Lys Asp Asn Thr Gln Asn
145                 150                 155

<210> SEQ ID NO 11
<211> LENGTH: 148
<212> TYPE: PRT
<213> ORGANISM: Cicer arietinum

<400> SEQUENCE: 11

Met Val Leu Leu Ile Ser Phe Glu Val Ser Ala Arg Asp Leu Thr Glu
1               5                   10                  15

Thr Ser Ser Asn Thr Glu Lys Glu Val Ala Glu Gln Lys Asn Glu Val
            20                  25                  30

Asn Asp Val Lys Tyr Gly Gly Gly Asn Tyr Gly Asn Gly Gly Gly Asn
            35                  40                  45

Tyr Gly Gln Gly Gly Gly Asn Tyr Gly Asn Gly Gly Asn Tyr Gly
        50                  55                  60

His Gly Gly Gly Asn Tyr Gly Asn Gly Gly Asn Tyr Gly His Gly
65                  70                  75                  80

Gly Gly Asn Tyr Gly Asn Gly Gly Asn Tyr Gly His Gly Gly
                85                  90                  95

Asn Tyr Gly His Gly Gly Asn Tyr Gly Asn Gly Gly His Gly Gly
            100                 105                 110

His Gly Gly Gly Tyr Cys Gly Asn Gly Cys Cys Gly Gly Tyr Tyr Ser
        115                 120                 125

Gly Ser Cys Arg Arg Cys Cys Ser Tyr Val Gly Glu Ala Ile Asp Val
        130                 135                 140
```

```
Asn Thr Leu Asn
145

<210> SEQ ID NO 12
<211> LENGTH: 7
<212> TYPE: PRT
<213> ORGANISM: Lilium

<400> SEQUENCE: 12

Tyr Pro Gly Gly Gly Gly Gly
1               5

<210> SEQ ID NO 13
<211> LENGTH: 6
<212> TYPE: PRT
<213> ORGANISM: Lilium

<400> SEQUENCE: 13

Tyr His Asn Gly Gly Gly
1               5
```

ISOLATED NUCLEIC ACID MOLECULE ENCODING A GLYCINE-RICH POLYPEPTIDE

BACKGROUND OF THE INVENTION

1. Field of the Invention

The present invention relates to a new gene encoding a glycine-rich polypeptide, and an expression vector, host cell and transgenic plant comprising the gene.

2. Description of the Prior Art

Plants have evolved many mechanisms against pathogen attack such as hypersensitive response (HR), systemic acquired resistance (SAR), and induced systemic resistance (ISR). SAR is evolved to defend pathogens in wide spectrum that is associated with sophisticated physiological and biochemical changes in plants (Ryals et al., 1996, Plant Cell 8: 1809–1819). SAR can be induced either by phytopathogens or chemicals (Kessmann et al., 1994, Annu. Rev. Phytopathol. 32: 439–459). In the pathogen-induced SAR, pathogens such as viruses, bacteria and fungi cause a cell death response and activate SAR in plants. As to the chemical-induced SAR, salicylic acid and probenazole are two representative chemicals for inducing SAR. For example, salicylic acid (SA), which is a well-known SAR inducer, plays an important role in the induction of plant defense. The researches with nahG transgenic plants suggest that SA is required for the development of SAR and has been reported to act as a secondary signal to elicit plant defense responses, as described in Metraux, 2001, Eur. J. Plant Pathol. 107: 13–18. Midoh and Iwata indicated that the probenazole induced the expression of defense-related genes (Midoh and Iwata, 1997, J. Pesticide Sci. 22: 45–47). Yoshioka et al. described that probenazole induced systemic acquired resistance in Arabidopsis with a novel type of action (Yoshioka et al., 2001, Plant J. 25: 149–157).

The accumulation of a group of proteins called pathogenesis-related proteins (PR proteins) correlates with the onset of SAR. The induction of PR proteins is considered to be the components of biochemical defenses. The PR proteins include PR1, β-1,3-glucanase, chitinases, lysozymes, PR4, thaumatin-like proteins, osmotin-like proteins, cysteine-rich proteins, glycine-rich proteins, proteinase inhibitors, proteinases, peroxidases, etc., which can build up the capability of disease resistance in plants to defend pathogen attack (Agrios G. N., 1997, Plant pathology, Academic press, San Diego, USA; Linthorst, 1991, Critical Rev. Plant Sci. 10:123–150). The expression of many defense-related genes during elicitation of SAR have been demonstrated. It is suggested that the genes are involved in both of biochemical and structural defenses of plants. It is believed that SAR-induced genes can enhance a plant's resistance to fungal attack.

SUMMARY OF THE INVENTION

The present invention provides an isolated nucleic acid molecule, which encodes a glycine-rich polypeptide comprising the amino acid sequence of SEQ ID NO: 2.

The present invention provides an expression vector comprising the isolated nucleic acid molecule of the invention.

The present invention also provides a host cell comprising the isolated nucleic acid molecule of the invention.

The present invention also provides a transgenic plant, which is transformed with the isolated nucleic acid molecule of the invention.

DETAILED DESCRIPTION OF THE INVENTION

Definitions

The term "nucleic acid molecule" refers to a polynucleotide such as deoxyribonucleic acid (DNA), and, where appropriate, ribonucleic acid (RNA). The term should also be understood to include, as equivalents, analogs of either RNA or DNA made from nucleotide analogs, and is applicable to the embodiments being described herein, single (sense or antisense) and double-stranded polynucleotides.

The term "amino acid sequence" refers to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule. An amino acid sequence includes an oligopeptide, peptide, polypeptide, or protein sequence, and fragments or portions thereof, and to naturally occurring or synthetic molecules.

The term "vector" refers to a nucleic acid molecule capable of transporting another nucleic acid to which it has been linked. Preferred vectors are those capable of autonomous replication and/or expression of nucleic acids to which they are linked. Vectors capable of directing the expression of genes to which they are operatively linked are herein referred to as "expression vectors". In general, expression vectors of utility in recombinant DNA techniques are often in the form of "plasmids," which generally refer to circular double stranded DNA loops, which are not bound to the chromosomes in their vector forms.

The term "host cell" refers to, for example, microorganisms including prokaryotic (Eubacteria and Archea) microorganisms (e.g., *E. Coli* and cyanobacteria) and eukaryotic microorganisms (e.g., yeast), and plant cells, which can be used as a recipient for introduction of a vector.

The term "transgene" refers to an exogenous coding region present in a host cell. A transgene is preferably transmitted to progeny cells.

The term "transgenic" refers to any cell, cell line, tissue, plant part or plant, the genotype of which has been altered by the presence of an exogenous coding region. Typically, the exogenous coding region was introduced into the genotype by a process of genetic engineering, or was introduced into the genotype of a parent cell or plant by such a process and is subsequently transferred to later generations by sexual crosses or asexual propagation.

Nucleic Acid and the Polypeptide Encoded Therefrom

The present invention relates to an isolated nucleic acid molecule which encodes a glycine-rich polypeptide comprising the amino acid sequence of SEQ ID NO: 2. Preferably, the isolated nucleic acid molecule has the sequence of SEQ ID NO: 1.

According to the invention, the glycine-rich polypeptide encoded by the nucleic acid of the invention comprises amino acid sequence of SEQ ID NO: 2. The sequence of SEQ ID NO: 2 has 138 amino acids, and contains a signal peptide with predicted cleavage site, a cysteine-rich C-terminus and several glycine stretches interspersed with Y, P, H, or N residues.

According to the invention, the isolated nucleic acid molecule encodes a glycine-rich polypeptide comprising the amino acid sequence of SEQ ID NO: 2 that shows high homology with several plant glycine-rich proteins (GRPs) belonging to Arabidopsis glycine-rich protein 3 superfamily. According to the nomenclature principles of plant GRPs, the glycine-rich polypeptide encoded by the nucleic acid of the invention is named LsGRP1 (Lilium oriental hybrid 'Star Gazer' glycine-rich protein 1). GRPs were considered to be cell wall structure proteins (Showalter et al., 1993, Plant Cell 5:9–23). The GRPs were reported to be accumulated in response to pathogen attack and play a role in the plant defense response (Molina et al., 1997, Plant Mol. Biol. 33:803–810). Therefore, the glycine-rich polypeptide encoded by the nucleic acid of the invention can be a cell wall structure protein that forms a barrier against pathogen attack such as fungi.

According to the invention, the expression of the glycine-rich polypeptide encoded by the nucleic acid of the invention is induced by SAR inducers, such as salicylic acid and probenazole, or pathogen, such as a fungus.

Expression Vector and Host System

The present invention also relates to an expression vector, which comprises the isolated nucleic acid of the invention. In order to express a nucleic acid molecule of the invention, the nucleic acid sequences encoding the glycine-rich protein of the invention comprising the amino acid sequence of SEQ ID NO: 2 or functional equivalents, can be inserted into an appropriate expression vector, i.e., a vector which contains the necessary elements for the transcription and translation of the inserted coding sequence. According to the invention, methods well known to those skilled in the art can be used to construct expression vectors containing sequences encoding the glycine-rich protein of the invention comprising the amino acid sequence of SEQ ID NO: 2 and appropriate transcriptional and translational control elements. These methods include in vitro recombinant DNA techniques, synthetic techniques, and in vivo genetic recombination.

Another object of the invention is to provide a host cell containing the expression vector containing the nucleic acid molecule of the invention. According to the invention, a number of host systems can be utilized to contain and express sequences encoding the glycine-rich protein of the invention comprising the amino acid sequence of SEQ ID NO: 2. A variety of techniques are available for the introduction of the nucleic acid fragment into a host cell. However, the particular manner of introduction of the nucleic acid fragment into the host cell is not critical to the practice of the present invention, and methods that provide for efficient transformation can be employed. Transformation of bacterial host cells can be accomplished by, for instance, electroporation or calcium chloride treatment. Many methods can be used for the introduction of the nucleic acid fragment into a plant cell; for example, the use of liposomes, transformation using viruses or pollen, chemical enhancement of the direct uptake of DNA, microinjection, electroporation, high-velocity microprojectiles, or Agrobacterium-mediated transformation.

Transgenic Plant

The present invention also relates to a transgenic plant, which is transformed with an isolated nucleic acid molecule of the invention.

Methods of making a transgenic plant of the invention typically involve the transformation of a cell of a plant with isolated nucleic acid molecule, which encodes a glycine-rich polypeptide comprising the amino acid sequence of SEQ ID NO: 2. The nucleic acid fragment is typically carried by a vector. A vector can provide for further cloning (amplification of the nucleic acid fragment), i.e., a cloning vector, or for expression of the polypeptide encoded by a coding region, i.e., an expression vector. The vector includes, but is not limited to, plasmid vector, viral vector, artificial chromosome vector, etc. Optionally, the vector may be capable of existing independently or integrated into a chromosome. Typically, a vector can be a conventional vector capable of replication in a bacterial host, for instance, E. coli. In a plant cell, the vector can replicate independently, i.e., extrachromosomally, which can allow for a large number of vectors to be maintained and potentially result in higher polypeptide production, or can be integrated into the genomic DNA. Preferable the vector is integrated into the genomic DNA of a plant cell. Vectors are preferably circular, and can also be linear. Construction of suitable vectors employs standard ligation techniques known in the art.

The transgenic plant of the invention has a resistance to a wide variety of pathogens through the expression of the new gene of the invention. Particularly, the transgenic plant has a resistance to fungal infection. More particular, the transgenic plant has a resistance to Botrytis gray mold.

Utility

The isolated nucleic acid molecule of the invention is a new gene encoding a glycine-rich polypeptide that is a pathogenesis-related protein. The overexpression of the gene of the invention in the plant will increase the resistance against a wide variety of pathogens. In particular, the expression of the gene of the invention can suppress fungal diseases such as Botrytis gray mold,.

In addition, the expression of the isolated nucleic acid molecule of the invention can be used as a marker of SAR. When a pathogen is perceived by a host cell, a series of response can be activated. The SAR signal transduction pathway may contribute to the active defense of the host against the pathogen. Therefore, the proteins encoded by the SAR genes are causally associated with disease resistance (Ryals et al, 1996, Plant Cell 8: 1809–1819). Given the above, the polypeptide encoded by the isolated nucleic acid molecule of the invention can be used as a quantitative tool to analyze the SAR response and an indicator of pathogen infection.

The following Examples are offered by way of illustration and not by way of limitation.

EXAMPLES

Materials and Methods

Lily Planting and SA Treatment

The bulbs of Lilium oriental hybrid 'Star Gazer' were planted in pot with 1:3 perlite-culture soil (Bas Van Buuren, Netherland) in semi-open canopy for thirty days then used as test plants in all experiments. The cultivation of lily and the experimental condition were at 20–23° C.

For the RNA isolation used in cDNA subtraction, SA solution was dripped in the rhizosphere of lily plants at a concentration of 0.4 mmole per kg soil per day. Lily leaves were collected after treatment for three days. For the RNA isolation used in Northern blot analysis, SA solution at a concentration of 10 mM was dripped in the soil of lily plants on the third, seventh, or every day post SA-treatment The leaves of treated lily plants were collected and stored at −80° C.

Construction of Subtracted cDNA Library

Total RNA of lily was isolated following the procedures as described by Ausubel et al., (1995). Lily mRNA was purified from total RNA with Oligotex mRNA Mini Kit (Qiagene, Hilden, Germany). Distinctly expressed or suppressed genes after SA treatment were selected with PCR-select cDNA Subtraction Kit (Clontech, Calif., USA). The subtracted cDNAs were amplified with Advantage 2 PCR Enzyme System (Clontech, Calif., USA) and ligated to pGEMTeasy vector (Promega, Wis., USA), then transformed to *Escherichia coli* DH5α to generate the subtracted cDNA library.

Differential Screening of Subtracted Library by Dot Blot Hybridization

The subtracted cDNA library was amplified by colony PCR. The overnight cultures of bacterial colonies were suspended in sterile water and adjusted to a concentration of $10^7$ CFU/ml as PCR templates. The reagents added to a 0.2 ml PCR tube were 1× Taq buffer, 1.5 mM $MgCl_2$, 0.5 $\mu$M Nested primer 1 and Nested primer 2R, 0.2 mM dNTP, 1.5 units Taq polymerase, and 2 $\mu$l PCR template. The thermal cycles were one cycle of 95° C., 5 min, 35 cycles of 95° C., 1 min, 60° C., 2 min, and 72° C., 2 min, then one cycle of 72° C., 10 min. The PCR products were dotted onto nylon membrane (Amershan-Pharmacia, HK, China) and hybridized with cDNA probes prepared from SA-treated or untreated lily leaves.

The mRNAs were isolated from SA-treated or untreated lily leaves and labeled with Digoxigenin-11-dUTP (Roche, Mannheim, Germany) by reverse-transcription method. Reagents were added in the following order: 6 $\mu$l 5× cDNA reaction buffer, 0.5 mM dNTP mixture, 0.13 mM dTTP, 0.07 mM DIG-dUTP, 0.074 $\mu$g/$\mu$l oligo-p(dT)$_{15}$, 1.5 $\mu$g heat-denatured RNA, DEPC-treated $H_2O$, and 1.67 units/$\mu$l AMV reverse-transcriptase. Total reaction mixture was adjusted to 30 $\mu$l with DEPC-treated Mili-Q water and incubated at 42° C. for 90 minutes. One milliliter of 200 mM EDTA solution was added to terminate the labeling reaction.

Hybridization and Detection

The nylon membrane dotted with PCR products was crosslinked with UV-light, prehybridized for 1.5 hr in per-hybridization buffer [5×SSC, 2% blocking reagent (Roche, Mannheim, Germany), 0.1% N-lauryl sacrosine, 0.02% SDS, 50% formamide], then hybridized with DIG-labeled cDNA probes in hybridization buffer overnight. The membrane was washed twice in prewashing buffer I (2×SSC, 0.1% SDS) at room temperature, and twice in prewashing buffer II (0.1×SSC, 0.1% SDS) for 15 min at 60° C.

Then, the membrane was washed with washing buffer (100 mM maleic acid, 150 mM NaCl, 0.3% Tween 20, pH 7.5) for 5 min and transferred to blocking solution (1% blocking reagent in maleic buffer) for 30–60 min. After blocking procedure, the membrane was incubated in antibody solution (0.001% Anti-Digoxigenin-AP in blocking solution) for 30 min. After being washed with washing buffer twice, the membrane was sealed in a plastic bag and treated with CSPD solution (Roche, Mannheim, Germany). After incubation for 10 min, the signals were detected by exposing membrane to X-ray film (Amershan-Pharmacia, HK, China).

Sequencing Analysis

The differentially expressed clones were amplified with BigDye Terminator Cycle Sequencing Ready Reaction (Perkin-Elmer, Calif., USA) and sequenced with ABI310 DNA sequencer. The sequences were analyzed with BLASTA, FASTA, PILEUP, and TRANSLATE programs in Genetic Computer Group, Wisconsin package version 10.6 (GCG package), SPSCAN program in SeqWeb and ClustalX program.

Full Length Cloning of LS1 cDNA

Rapid amplification of cDNA end (RACE) was used to clone 5'-end of LsGRP1 cDNA. Total RNA of SA-treated lily leaves was extracted and purified to obtain mRNA by Oligotex mRNA Mini Kit (Qiagene, Hilden, Germany). The 5' end cDNA was obtained by reverse transcription of mRNA with Marathon cDNA Amplification Kit (Clontech, Calif., USA) and linkers were ligated to the both ends of cDNA. Primers on linker sequence and LS1 were used to amplify the full-length cDNA. The PCR products were ligated to the pGEMTeasy vector and screened the LsGRP1 cDNA containing-clones by dot blot hybridization. Full-length cDNA clones were sequenced with ABI 310 DNA sequencer and analyzed with GCG packages.

Probenazole Treatment

Granules of probenazole (6% active ingredient) (Taiwan San-Li, Taiwan, ROC) were directly applied to the rhizosphere of lily plants at a concentration of 40 mg a .i. per kg soil. On the seventh day after treatment, lily leaves were collected and stored at −80° C. before RNA extraction.

Pathogen Inoculation

The spore suspension of *Botrytis elliptica* strain B061-1 from 5-day culture on V8 juice slant was prepared by gently vortexing in the 0.1% Tween 20 solution. The concentration of spore suspension was adjusted to $10^5$ spores per ml. The spore suspension was atomized on the abaxial surface of lily leaves. Inoculated lily plants were incubated in moist chamber for different intervals. Inoculated and systemic upper leaves were collected and stored at −80° C. before RNA extraction.

Northern Blot Analysis

Total RNA isolation was performed with Plant Total RNA Miniprep Kit (Viogene, Taiwan, ROC). After formaldehyde gel electrophoresis, RNAs were transferred to a positive-charged nylon membrane by capillary method. Hybridization and detection were performed as described above.

Southern Blot Analysis

Genomic DNA of lily was extracted with Plant Genomic DNA Mini Kit (Viogene, Taiwan, ROC) and digested with restriction enzymes EcoRI, BamHI and HindIII. Digested DNA was separated by 1% gel electrophoresis. After washed with denaturation and neutralization buffer, DNA was transferred to nylon membrane by capillary method. Hybridization and detection was performed as described.

Results

Identification of Differentially Expressed Genes

Figure 1:
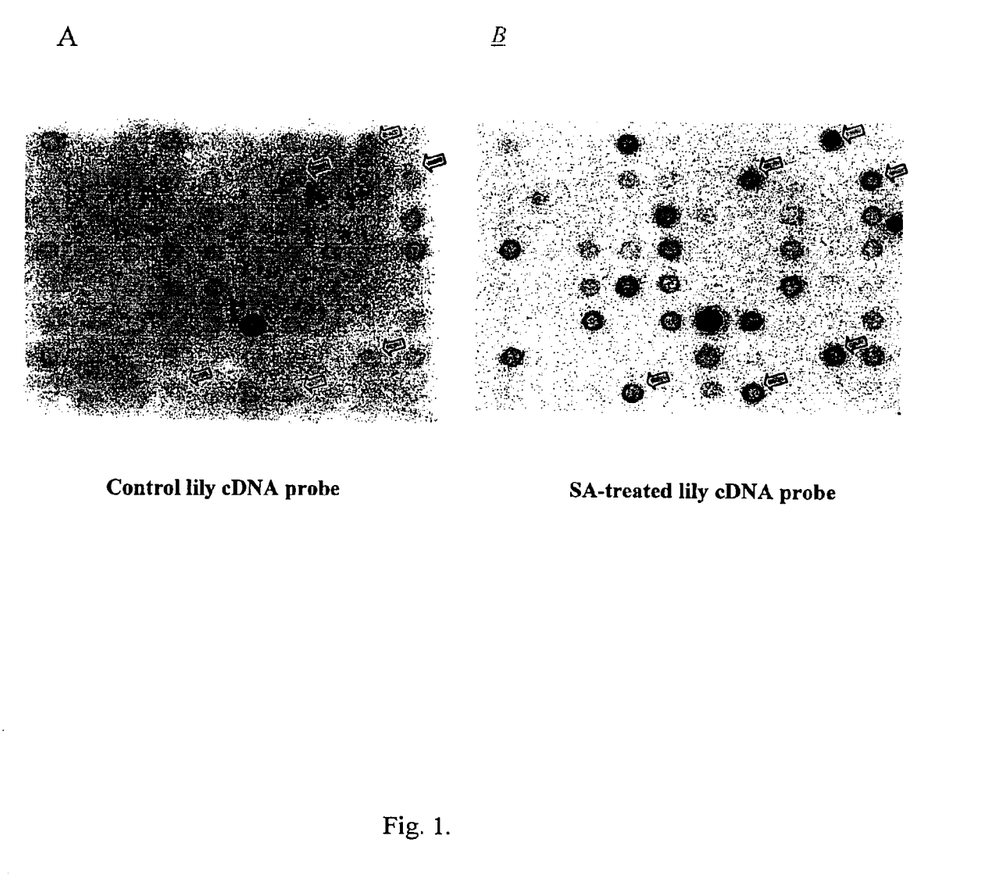
FIG. 1 shows the dot blot hybridization analysis of subtracted PCR products.

For cloning of SA-inducible gene of lily, PCR-select subtraction method was performed. By using this approach, differentially expressed mRNAs of lily genes were enriched, and then confirmed by comparison of the strength of hybridization signals after detection with cDNA probes derived from SA-treated and untreated lily mRNA. Among the analyzed clones of 612, six clones with distinct signals were selected (FIG. 1). The PCR products of subtractive cDNA library were dotted onto nylon membranes in the same order and detected with control lily cDNA probe (A) or SA-treated lily cDNA probe (B). Clones that were differentially expressed in SA-treated plants were indicated with arrows.

Sequence analysis showed that all these six clones had identical insert sequence that designated as LS1 (lily SA-induced).

Figure 2:
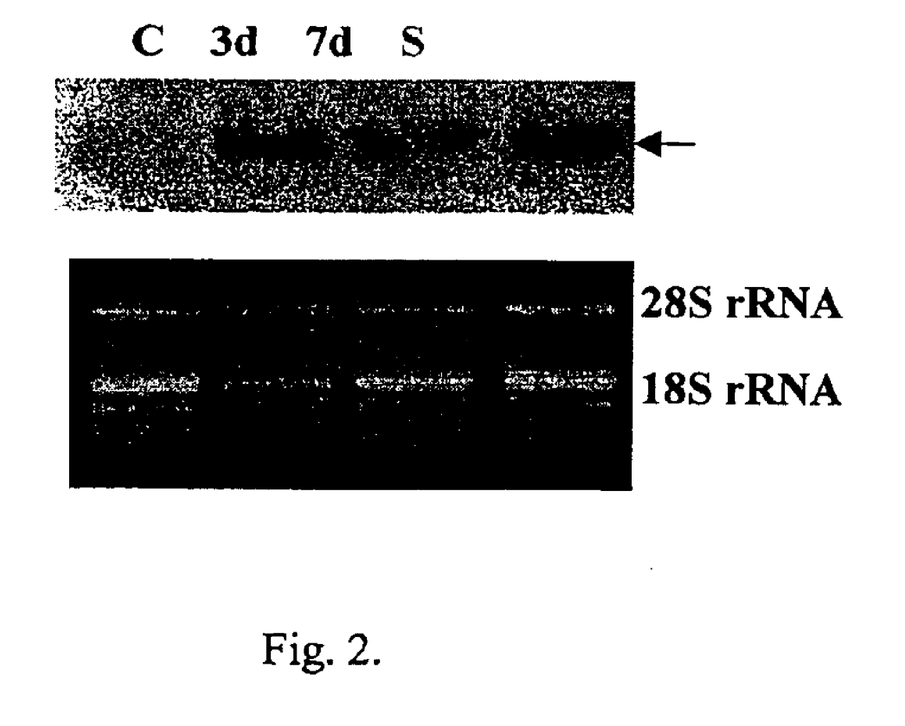
FIG. 2 shows the Northern blot analysis of LsGRP1 expression in SA-treated lily leaves.

SA solution was dripped in the rhizosphere of lily plants at a concentration of 0.4 mmole per kg soil. Northern blot analysis showed that the transcript of LS1 was increased on the third day after SA treatment and lasted for at least 7 days (FIG. 2). Total RNA was extracted from lily leaves that treated with SA for one, three and seven days before harvest (S). RNA from untreated lily leaves was used as a control (C). The blotted membrane was detected with DIG-labeled LS1 probe and signals were indicated with arrow. The rRNA in lower panel was a reference of the amount of total RNA loaded. The transcripts of LS1 were induced in treated leaves after spraying of SA on the abaxial surface of lily leaves; no significantly induction was found in systemic leaves.

Cloning of LsGRP1 Full-length cDNA and Sequence Analysis

Figure 3A:
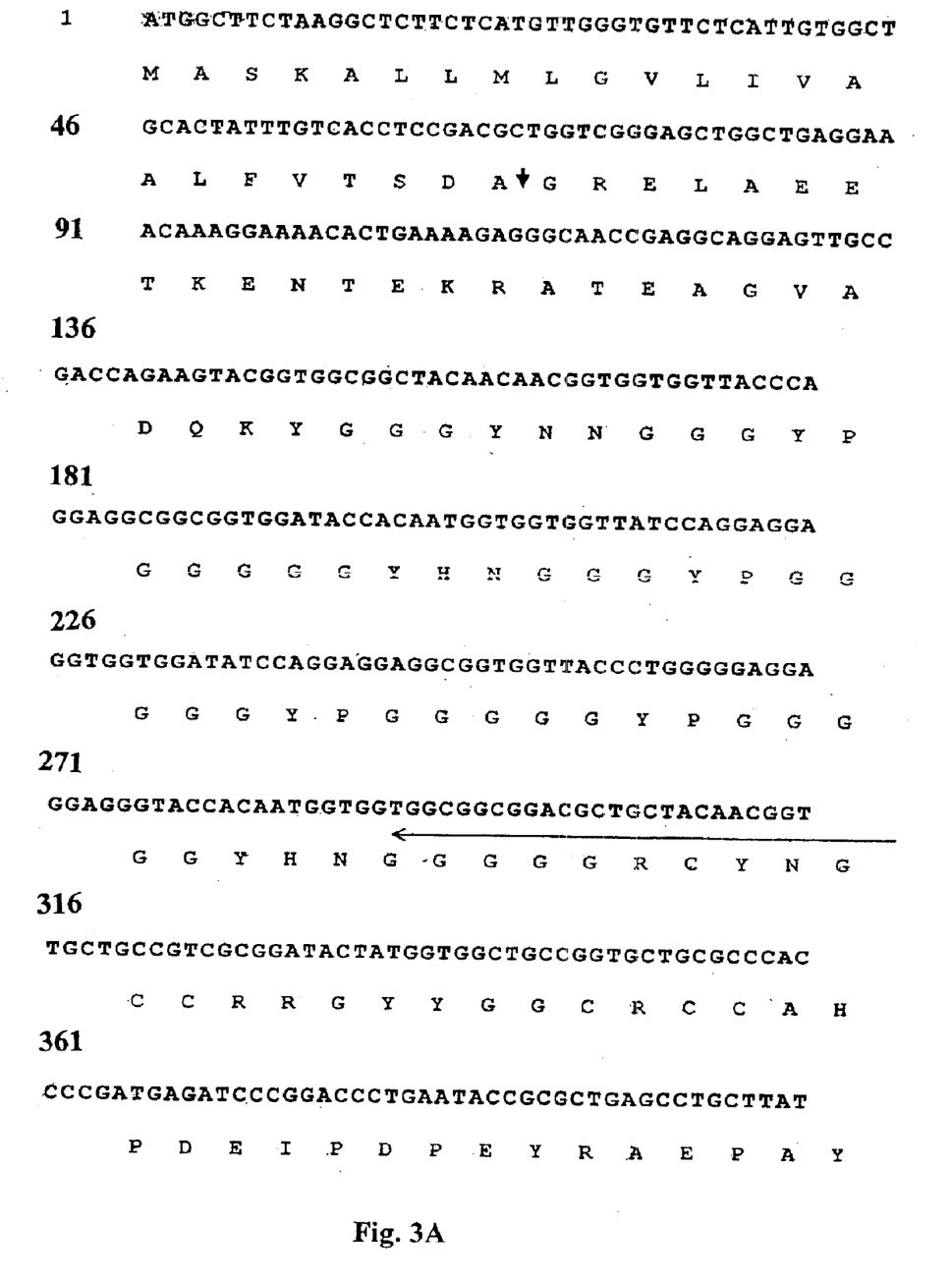
FIGS. 3A–3B show the nucleotide sequence of LsGRP1 cDNA (SEQ ID NO: 1).
Figure 3B:
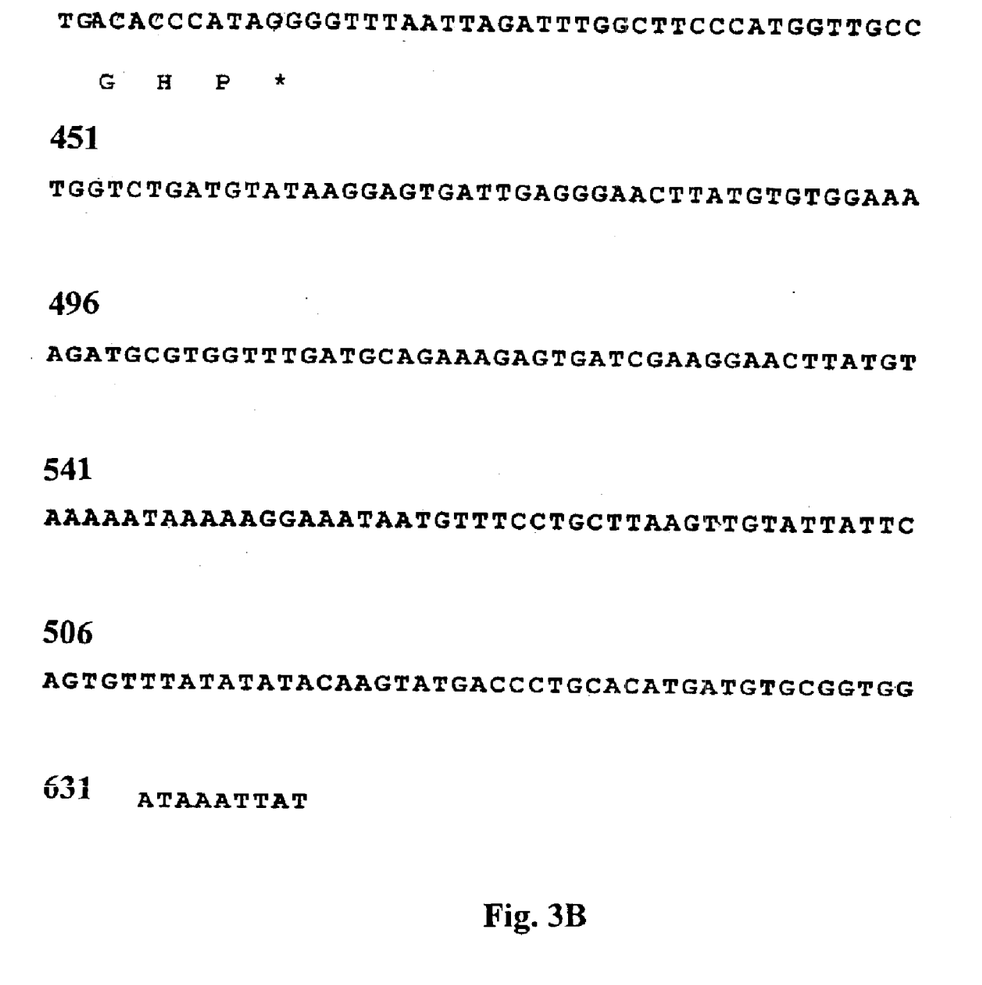

The LS1-specific primers were designed based on the partial nucleotide sequence of cloned LS1 fragment and used in the 5' RACE. Linkers-ligated SA-treated lily cDNA was generated and used as PCR template to amplify LS1 full-length cDNA (FIG. 3A–B). The sequence of the full-length LS1 cDNA was analyzed by TRANSLATE, FRAMES, and SPSCAN programs in Genetic Computer Group, Wisconsin Package Versin 10.3 (CGC, CA, USA) and SeqWeb packages. An open reading frame of 417 bp that encoding 139 amino acid was revealed (FIG. 3). The full-length LS1 protein contained 28.78% glycine residues and had a molecular weight of 11 kDa. The deduced amino acid sequence of LS1 contained signal peptide with predicted cleavage site, cysteine-rich C-terminus and several glycine stretches interspersed with Y, P, H, or N residues (FIG. 3A–B). The SPSCAN analysis also showed conserved cleavage site of signal peptides among nine compared GRPs. The glycine-rich stretches of full-length LS1 sequence showed repeating sequence of YPGGGGG (SEQ ID NO: 12) or YHNGGG (SEQ ID NO: 13) (FIG. 3A–B). FASTA analysis showed that full-length sequence of LS1 shares 52.0–62.2% similarity to the glycine-rich proteins (GRPs) of several plants such as alfalfa, arabidopsis, barley, carrot, chickpea, and tobacco. These GRPs described belonged to Arabidopsis glycine-rich protein 3 superfamily (Table 1).

TABLE 1

| Accession No. | % Similarity | Sources | Descriptions |
| --- | --- | --- | --- |
| Jq1062 | 62.21 | Arabidopsis thaliana | Differentially expressed, glycine-rich protein |
| S04069 | 59.69 | Chenopodium rubum | Glycine-rich protein |
| S10334 | 57.85 | Hordeum vulgare | Pathogen-responsive, glycine-rich protein |
| S35716 | 56.49 | Daucus carota | Embryogenesis-related, glycine-rich protein |
| E84469 | 56.06 | Arabidopsis thaliana | Glycine-rich protein |
| S18345 | 52.00 | Medicago sativa | Cell wall structural glycine-rich protein |
| T06256 | 53.23 | Pisum sativum | Glycine-rich protein |
| T09527 | 53.85 | Cicer arietinum | Cell wall structural glycine-rich protein |
| T03257 | 52.78 | Nicotiana tabacum | Glycine-rich protein |

Figure 4:
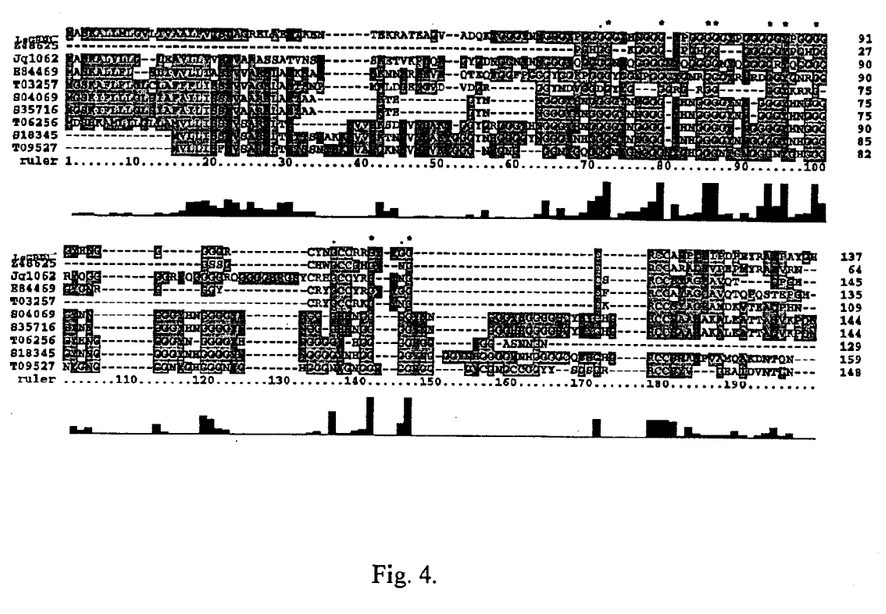
FIG. 4 shows the alignment of the deduced amino acid sequence of LsGRP1 (SEQ ID NO:2) with that of other plant GRPs, namely Z486625 (SEQ ID NO:3) Jq 1062 (SEQ ID NO:4); E84469 (SEQ ID NO:5); T03257 (SEQ ID NO: 6); S04069 (SEQ ID NO: 7); S35716 (SEQ ID NO: 8); T06256 (SEQ ID NO: 9); (SEQ ID NO: 10); and T09527 (SEQ ID NO:11).

Herein, LS1 was renamed as LsGRP1 (Lilium oriental hybrid 'Star Gazer' glycine-rich protein 1) which referred to the nomenclature of plant GRPs. Alignment of LsGRP1 to other GRPs with PILEUP program in GCG package and realignment with ClustalX program revealed similar hydrophobic amino acids composition of signal sequences (FIG. 4).

LsGRP1 Expression Induced by Probenazole

Figure 5:
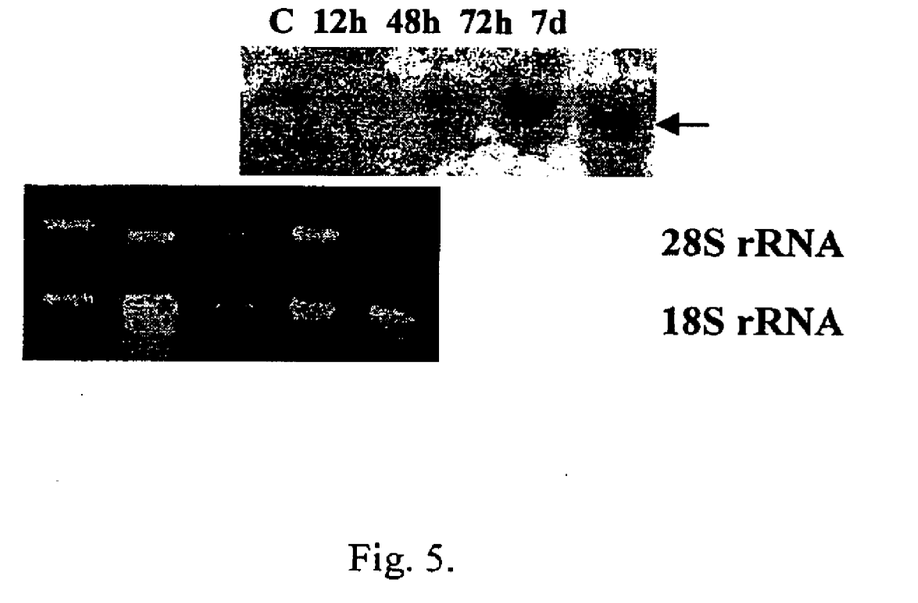
FIG. 5 shows the Northern blot analysis of RNA transcript of LsGRP1 in probenazole-induced lily leaves.

Probenazole have been used to induce the systemic resistance of lily against the infection of B. elliptica (Lu & Chen, 1998). The transcription level of LsGRP1 was increased after probenazole treatment. The induction of LsGRP1 was not detected at 12 hr post treatment. However, a significant increase in the transcripts of LsGRP1 appeared at 48 hr post treatment of probenazole, and the expression level reached the highest level at 72 hr, then the transcripts of LsGRP1 slightly declined at the seventh day post probenazole treatment (FIG. 5).

The granules of probenazole were applied in the rhizosphere of lily plants at a concentration of 40 mg per kg soil. Total RNA was harvested from lily leaves after treated for 12 hours (12h), 48 hours (48 h), 72 hours (72 h), or seven days (7 d). RNA from untreated lily leaves was used as a control (C). The blotted membrane was detected with DIG-labeled LsGRP1 probe and signal was indicated with an arrow. The rRNA in the lower panel was a reference of the amount of total RNA loaded. Overall, the expression of LsGRP1 could last for at least 15 days post treatment of probenazole.

LsGRP1 Expression Systemically After Pathogen Infection

Figure 6:
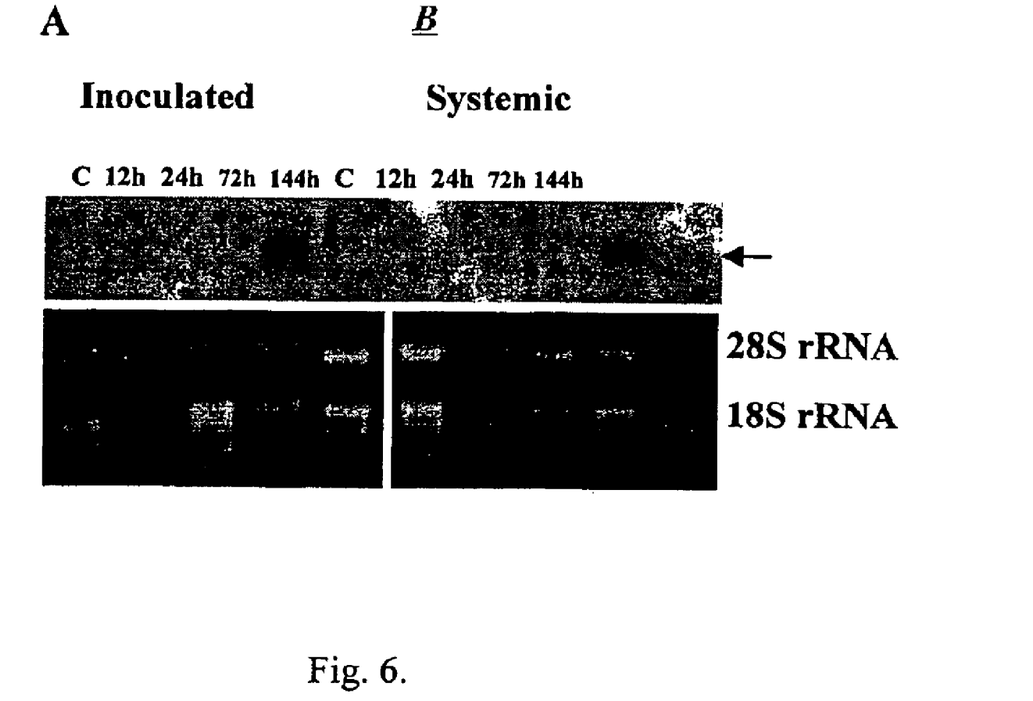
FIGS. 6A–6B show the Northern blot analysis of RNA transcript of LsGRP1 in *Botrytis elliptica*-inoculated lily plants.

The LsGRP1 expression after B. elliptica-inoculation was examined in Northern blot analysis. The LsGRP1 transcripts were slightly induce in the B. elliptica-treated leaves at 32 hr post inoculation, reached the maximum level at the third day post inoculation. However, the induction of LsGRP1 was not detected at the sixth day post inoculation (FIG. 6A–B). Besides that, LsGRP1 transcripts also increased in the systemic leaves in a similar temporal pattern as that displayed in the inoculated leaves (FIG. 6A–B). The leaves of lily plants were inoculated with the spore suspension of B. elliptica. Total RNA were extracted from inoculated (A) and systemic (B) lily leaves at 12 hours (12 h), 24 hours (24 h), 72 hours (72 h), or 144 hours (144 h) post inoculation. RNA from untreated lily leaves was used as control (C). The blotted membrane was detected with DIG-labeled LsGRP1 probe and signals were indicated with arrows. The rRNA in lower panel was a reference of the amount of total RNA loaded.

PCR and Southern Blot Analysis of LsGRP1

Using the lily genomic DNA as template, a single PCR product of 417 bp was amplified by a pair of gene-specific primers. The PCR product of LsGRP1 was confirmed by dot blot hybridization. The Southern blot analysis indicated that LsGRP1 seems to be a single copy gene in the genome of Lilium oriental hybrid 'Star Gazer'.

What is claimed is:

1. An isolated nucleic acid molecule, which encodes a glycine-rich polypeptide comprising the amino acid sequence of SEQ ID NO: 2.

2. The isolated nucleic acid molecule of claim 1, which has the sequence of SEQ ID NO: 1.

3. An expression vector comprising the isolated nucleic acid molecule as claimed in claim 1.

4. The expression vector of claim 3, wherein the isolated nucleic acid molecule has the sequence of SEQ ID NO: 1.

5. A host cell comprising the expression vector of claim 3.

6. A host cell comprising the expression vector of claim 4.

7. The host cell of claim 6, wherein the host cell is a bacterial cell or a plant cell.

8. The host cell of claim 7, wherein the bacterial cell is an *Agrobacterium* cell.

9. The host cell of claim 7, wherein the host cell is a plant cell.

10. A transgenic plant, which is transformed with the isolated nucleic acid molecule of claim 1.

11. The transgenic plant of claim 8, which is transformed with the isolated nucleic acid molecule of claim 2.

* * * * *